(12) United States Patent
Saunders et al.

(10) Patent No.: US 9,220,273 B2
(45) Date of Patent: *Dec. 29, 2015

(54) INSECTICIDAL COMPOSITIONS AND METHODS OF USING THE SAME

(71) Applicant: Clarke Mosquito Control Products, Inc., St. Charles, IL (US)

(72) Inventors: Marie Elizabeth Saunders, Schaumburg, IL (US); Jonathan David Ostrowski, Chicago, IL (US); Michael Dean Willis, Elgin, IL (US); Darryl Ramoutar, St. Charles, IL (US); Joanna Maria Tyszko, Hanover Park, IL (US)

(73) Assignee: Clarke Mosquito Control Products, Inc., St. Charles, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/656,929

(22) Filed: Mar. 13, 2015

(65) Prior Publication Data

US 2015/0181886 A1 Jul. 2, 2015

Related U.S. Application Data

(63) Continuation of application No. 13/220,458, filed on Aug. 29, 2011, now Pat. No. 8,980,341.

(51) Int. Cl.
| | | |
|---|---|---|
| *A61K 36/889* | (2006.01) |
| *A01N 59/00* | (2006.01) |
| *A01N 61/02* | (2006.01) |
| *A01N 25/00* | (2006.01) |
| *A01N 31/14* | (2006.01) |
| *A01N 65/40* | (2009.01) |
| *C02F 1/68* | (2006.01) |
| *C02F 103/00* | (2006.01) |

(52) U.S. Cl.
CPC .............. *A01N 59/00* (2013.01); *A01N 25/00* (2013.01); *A01N 31/14* (2013.01); *A01N 61/02* (2013.01); *A01N 65/40* (2013.01); *C02F 1/68* (2013.01); *C02F 2103/007* (2013.01)

(58) Field of Classification Search
CPC ........................... A61K 36/889; A61K 9/2036
USPC .......................................... 424/405, 725, 727
See application file for complete search history.

(56) References Cited

U.S. PATENT DOCUMENTS

| | | | |
|---|---|---|---|
| 3,222,201 A | 12/1965 | Boyle et al. |
| 3,222,213 A | 12/1965 | Clark et al. |
| 3,457,109 A | 7/1969 | Peist et al. |
| 4,569,947 A | 2/1986 | Stockton et al. |
| 4,707,359 A | 11/1987 | McMullen |
| 5,273,967 A | 12/1993 | Pittendrigh |
| 6,512,012 B1 | 1/2003 | Levy |
| 6,872,736 B1 * | 3/2005 | Aven .............................. 514/359 |
| 7,807,717 B2 | 10/2010 | Newman |
| 2002/0107149 A1 * | 8/2002 | Volgas et al. .................. 504/317 |
| 2009/0069183 A1 | 3/2009 | Stringfellow |

OTHER PUBLICATIONS

Itaki et al., "Laboratory Evaluation of Traditionally made Coconut Oil as a Surface Larvacide for Malaria Vector Control," Contemporary PNG Studies: DWU Research Journal vol. 12, May 2010, 92-99.
Foley et al., "Laboratory Evaluation of Methylated Coconut Oil as a Larvicide for Anopheles Farauti and Culex Annulirostris," Journal of the American Mosquito Control Association, 21(4):477-479, 2005.

* cited by examiner

*Primary Examiner* — Christopher R Tate
*Assistant Examiner* — Deborah Davis
(74) *Attorney, Agent, or Firm* — Michael Best & Friedrich LLP

(57) ABSTRACT

Provided are mosquito larvicide compositions comprising a mineral oil and a methylated coconut oil. The compositions may further comprise a silicone and at least one surfactant. The compositions can kill mosquito larvae in swamps, floodwater areas, and other areas where mosquitoes develop. Further provided are methods for mosquito control. The methods may comprise coating the surface of a body of water.

17 Claims, No Drawings

INSECTICIDAL COMPOSITIONS AND METHODS OF USING THE SAME

CROSS-REFERENCE TO RELATED APPLICATIONS

This application is a continuation of and claims priority to co-pending U.S. patent application Ser. No. 13/220,458 filed Aug. 29, 2011, the entire content of which is incorporated herein by reference.

FIELD

The disclosure relates to compositions and methods useful for insect control.

BACKGROUND

Over one billion tons of pesticide products are used each year in the United States. Pesticides are an important component of pest management strategies in the public health industry. The Environmental Protection Agency (EPA) Office of Pesticide Programs registers and regulates pesticides as mandated by Federal Law. One of their mandates is to approve safer, reduced risk pesticides.

Currently there are many established methods for controlling the development of juvenile mosquito life stages, that is, both larvae and pupae, in the aquatic environment. One widely accepted procedure involves coating the surface of a body of water with a uniform film that acts to reduce the water's surface tension. This mode-of-action prevents larvae from accessing atmospheric oxygen, as their breathing siphons are inhibited from attaching to the surface of treated water and/or leading to a saturation of their tracheal systems; larval death occurs as a result of either drowning or suffocation. In addition, surface films may also impede adult mosquitoes from laying eggs.

Compositions that coat the surface of a body of water can kill mosquito larvae, that is, act as a larvicide. The compositions may also act as a larvicide without including any traditional pesticide. Because the mode of action is physical rather than chemical, mosquitoes cannot easily develop resistance.

U.S. Pat. No. 4,569,947 describes a method for controlling mosquitoes, which comprises coating the surface of a body of water containing immature forms of mosquitoes with an effective amount of one or more of a β-branched alkanol or a 1-3 mole alkoxylate thereof.

U.S. Pat. No. 4,707,359 describes a composition for controlling the breeding of insects (particularly mosquitoes) that have aquatic breeding sites. The composition comprises two components. The first component is an insoluble monomolecular layer, an insoluble foam layer, or a duplex film layer. The second component comprises a mosquito larva toxin obtained during growth of bacterial cultures. The combination of the two components provides a synergistic mixture.

U.S. Pat. No. 5,273,967 describes a method for killing immature mosquitoes in a body of water comprising spreading on the surface of the body of water a particulate, solid carbohydrate compound. The compound is non-soluble in water. The compound is spread in a quantity sufficient to hydrate at the surface of the body of water and form a substantially unbroken, floating hydrated carbohydrate layer, thereby suffocating the mosquitoes in the body of water.

U.S. Pat. No. 6,512,012 describes a method of controlling the population of mosquitoes comprising applying a surface-active composition to an aquatic environment to form a film over water within that environment. The compositions comprise at least one $C_6$ to $C_{11}$ alcohol alkoxylate.

U.S. Pat. No. 7,807,717 a method for the control of insects breeding on water surfaces. The methods consist essentially of blending in a high shear mixer the ester of a fatty acid of 10 to 25 carbon atoms, a low molecular weight alcohol, an emulsifying agent, a thickener, and water. The composition is applied to the surface of insect infested water and forms an oil film on the water.

Many types of insecticides have been used to kill mosquitoes and other insect pests. Nevertheless, many insecticides have disadvantages. Some are toxic to humans, are harmful to the environment, or have limited efficacy. Accordingly, there is a continuing need for environmentally friendly compounds having improved insecticidal properties, while being substantially non-toxic or only mildly toxic to humans.

For example, some insecticides include organic solvents, in particular, aromatic hydrocarbons, chlorinated hydrocarbons, aliphatic hydrocarbons or petroleum distillates, which in high concentrations can be hazardous to human health. As such, the replacement of a majority of an aliphatic hydrocarbon with an alternate oil is desirable.

SUMMARY

In some aspects, provided are compositions comprising mineral oil, methylated coconut oil, at least one surfactant, and silicone.

In other aspects, provided are methods for controlling insects, the methods comprising controlling the development of mosquitoes in aquatic breeding habitats with a composition comprising mineral oil, methylated coconut oil, at least one surfactant, and silicone.

In other aspects, provided are methods for mosquito control comprising administering a composition comprising mineral oil, methylated coconut oil, at least one surfactant, and silicone to a surface of a body of water. The compositions can form a coating on the surface of the water.

In other aspects, provided are methods for controlling mosquitoes, the methods comprising forming a surface film over a body of water with a composition comprising mineral oil, methylated coconut oil, at least one surfactant, and silicone.

Other aspects of the disclosure will become apparent by consideration of the detailed description.

DETAILED DESCRIPTION

The disclosure broadly relates to insecticidal compositions and methods of using the same. The compositions and methods may be effective and selective in killing insects. In some aspects, the compositions comprise a mineral oil, a methylated coconut oil, at least one surfactant, and silicone. While individually these ingredients may not provide significant insecticidal activity, a combination of these ingredients provides a safe and efficacious insecticidal composition. The compositions described herein may be formulated for application or delivery to a surface and can form a uniform film or coating on the surface, such as the surface of a body of water. The compositions can reduce the surface tension of water and thereby prevent larvae from accessing the air and also inhibit adults from laying eggs.

Compositions

Compositions described herein may comprise a mineral oil, a methylated coconut oil, at least one surfactant, and silicone, which in combination provides enhanced insecticidal activity compared to a conventional surface film. It has unexpectedly been found that these components, when tested alone, do not provide any level of biological control, but when combined according to the present disclosure, provide an effective treatment for killing mosquito larvae without the use of a chemical toxicant.

"Mineral oil" as used herein relates to the commonly known product of the same name, which is a by-product of the distillation of petroleum (crude oil) to make gasoline, cosmetics, pharmaceuticals, and many other products. Synonymous names for mineral oil can include "paraffin oil" or "white mineral oil" among other common names. Mineral oil is available from any number of commercial distributors (e.g., Brenntag, Barton Solvents). Non-limiting examples of "mineral oil" include those identified by CAS registry numbers: 8012-95-1, 8020-83-5, 8042-47-5, 72623-84-8, 72623-86-0, 72623-87-1, 64741-88-4, 64741-89-5, 64742-54-7, 64742-55-8, 64742-56-9, and 64742-65-0. White mineral oil is typically transparent and colorless and comprises complex mixtures of long chain aliphatic compounds often ranging in size from $C_{15}$-$C_{40}$. It is also used in cosmetics, pharmaceuticals, suntan lotions, baby oils, bath oils, and as a base for ointments. Various grades of mineral oil may have a viscosity in the range of about 70 Saybolt Universal Seconds or SUS to 550 SUS at 40° C. Depending on the refining process and source of crude oil, mineral oils can also include paraffinic, naphthenic, and aromatic compounds in varying weight percentages.

The compositions may comprise mineral oil in an amount of at least about 1%, at least about 2%, at least about 3%, or at least about 5% by weight of the composition. The compositions may comprise mineral oil in an amount of less than about 20%, less than about 18%, less than about 16%, or less than about 15% by weight of the composition. The compositions may comprise mineral oil in an amount of about 1% to about 20%, about 2% to about 18%, about 3% to about 16%, or about 5% to about 10% by weight of the composition.

While the specifications for mineral oil used in the cosmetic and pharmaceutical industry are very well defined, these same specifications (that assessed quality) are not always helpful in defining a mineral oil that provides an efficacious composition in the surface treatment of mosquito larvae. A series of six different lots of mineral oil were analyzed in a blind study by three different laboratories and were determined to be "nearly identical." As shown in Example 2, however, these same lots produced significantly different levels of percent mortality when formulated with a surfactant (ethoxylated alkylphenol) and a dispersing agent (silicone).

The compositions described herein overcome mineral oil's variable efficacy in controlling mosquitoes. It was discovered that the inclusion of a coconut oil in the compositions reduces the variability in efficacy, as shown in Example 4. As further detailed in Example 12, compositions comprising methylated coconut as described herein are effective in controlling mosquitoes, regardless of which lot of mineral oil is used. Further, it was surprisingly discovered that addition of a methylated coconut oil significantly reduces the weight percent of mineral oil needed to maintain an efficacious treatment for mosquito control, as shown in Example 4.

The compositions described herein comprise methylated coconut oil, also referred to herein as a methyl ester of coconut oil. "Coconut oil" as used herein relates to the edible oil extracted from the kernel or meat of matured coconut harvested from the coconut palm (*Cocos nucifera*) and derivatives of these oils. Coconut oils include, but are not limited to, coconut oil, virgin coconut oil, refined coconut oil, and methyl esters of coconut oil. Commercial methyl esters such as methylated coconut oil (MCO) are made from naturally occurring edible fats and oils. The refined oil of these molecules is converted to a methyl ester through esterification with methanol and a base catalyst. Methyl esters can be fractionated into various alkyl range cuts (light, mid, and heavy) by distillation. As they are used in a wide range of direct and indirect food applications, the safety of the methyl esters is recognized by the US EPA, the Flavor and Extract Manufacturers Association, and the U.S. Food and Drug Administration.

The compositions may comprise coconut oil in an amount of at least about 50%, at least about 60%, or at least about 70% by weight of the composition. The compositions may comprise coconut oil in an amount of less than about 99%, less than about 95%, or less than about 90% by weight of the composition. The compositions may comprise coconut oil in an amount of about 50% to about 99%, about 60% to about 95%, about 70% to about 90%, or about 75% to about 95% by weight of the composition.

For example, in some embodiments, compositions may comprise about 8-12% mineral oil and about 80-90% methylated coconut oil.

Compositions may further comprise silicone. Silicones may include, but are not limited to, polydimethylsiloxane (polymerized silicone), silicone emulsions, and modified silicones. They can be effective across a wide temperature range and can align functional groups across interfaces such as water/air and water/oil. A silicone may contribute to the spreading of the composition on a surface when used with a surfactant. This allows for a thinner and more uniform film of the composition to be applied to a surface. Silicone may act at the surface or water/air interface, and hence, silicone may be referred to as a surface active agent. Polymerized silicones such as polydimethylsiloxane are inert and non-reactive and therefore provide a level of safety when used in a composition.

The compositions may comprise silicone in an amount of at least about 0.1%, at least about 0.2%, or at least about 0.3% by weight of the composition. The compositions may comprise silicone in an amount of less than about 5.0%, less than about 4.0%, or less than about 3.0% by weight of the composition. The compositions may comprise silicone in an amount of about 0.1% to about 5.0%, about 0.2% to about 4.0%, or about 0.3% to about 3.0% by weight of the composition.

For example, in some embodiments, compositions may comprise about 8-12% mineral oil, about 80-90% methylated coconut oil, and about 0.2-0.4% polydimethylsiloxane.

Compositions may further comprise at least one surfactant. Surfactants may include, but are not limited to, nonionic surfactants, anionic surfactants, cationic surfactants, and amphoteric surfactants. In some suitable embodiments, the surfactant is a nonionic surfactant.

Examples of nonionic surfactants include, but are not limited to, amides, alkanolamides, amine oxides, block polymers, alkoxylated primary and secondary alcohols, alkoxylated alkylphenols, alkoxylated fatty esters, sorbitan derivatives, glycerol esters, propoxylated and alkoxylated fatty acids, alcohols, alkyl phenols, and glycol esters. For example, nonionic surfactants may include, but are not limited to, ethoxylated tridecyl alcohol, sorbitan monooleate, sorbitan monolaurate, and sorbitan monostearate.

Examples of anionic surfactants include, but are not limited to, sulfosuccinates and derivatives, sulfates of ethoxylated alcohols, sulfates of alcohols, sulfonates and sulfonic acid derivatives, sulfates and sulfonates of alkoxylated alkylphenols, phosphate esters, and polymeric surfactants. Suitably, anionic surfactants may include, but are not limited to, alkyl sulfates, ether sulfates, alkyl benzene sulfonates, alpha olefin sulfonates, diphenyloxide disulfonates, alkyl naphthalene sulfonates, sulfosuccinates, sulfosuccinamates, naphthalene-formaldehyde condensates, isethionates, N-methyl taurates, phosphate esters, and ether carboxylates.

Cationic surfactants may include amine surfactants, those containing non-quaternary nitrogen, those containing quaternary nitrogen bases, those containing non-nitrogenous bases and combinations of these surfactants. Such surfactants are disclosed in U.S. Pat. No. 3,457,109; U.S. Pat. No. 3,222,201; and U.S. Pat. No. 3,222,213, which are hereby fully incorporated by reference. Additional cationic surfactants may include ditallowalkyldimethyl (or diethyl or dihydroxyethyl) ammonium chloride, ditallowalkyldimethylammonium methyl sulfate, dihexadecylalkyl (C16) dimethyl (or diethyl, or dihydroxyethyl) ammonium chloride, dioctodecylalkyl (C18) dimethylammonium chloride, dieicosylalkyl (C20) dimethylammonium chloride, methyl (1) tallowalkyl amido ethyl (2) tallowalkyl imidazolinium methyl sulfate (commercially available as Varisoft 475 from Ashland Chemical Company), or mixtures of those surfactants. Other cationic surfactants may include sulfonium, phosphonium, and mono- or tri-long-chain quaternary ammonium materials.

Amphoteric surfactants may include zwitterionic surfactants. Amphoteric surfactants may also include, but are not limited to, amphoteric imadazoline derivatives and fatty amine and fatty amine ethoxylate derivatives. Amphoteric imadazoline derivatives may include, but are limited to, amphodiacetates, amphoacetates, amphocarboxylates, amphopropionate, amphodipropionate, and hydroxypropyl sulfonate. Fatty amine and fatty amine ethoxylate derivatives may include, but are not limited to, betaines, alkyl betaine, sultaine, dihydroxyethyl glycinate, alkyl amidopropyl betaine, and aminopropionate.

The hydrophilic-lipophilic balance (HLB) system is a useful expression of the hydrophilic (polyhydric alcohol or ethylene oxide) and the lipophilic (fatty acid or fatty alcohol) characteristics of a surfactant molecule. On an arbitrary scale of 1-20 (assigned by Atlas Chemical in the 1940's), a low HLB is considered lipophilic or oil-soluble. A high HLB is considered hydrophilic or water-soluble. An HLB of 9-11 is considered to be intermediate. HLB can provide invaluable insight in the selection of an appropriate surfactant for the desired properties of the compositions.

The compositions may comprise surfactant in an amount of at least about 1%, at least about 2%, or at least about 10% by weight of the composition. The compositions may comprise surfactant in an amount of less than about 10%, less than about 8%, or less than about 6% by weight of the composition. The compositions may comprise surfactant in an amount of about 1% to about 10%, about 2% to about 8%, or about 3% to about 6% by weight of the composition.

For example, in some embodiments, compositions may comprise methylated coconut oil, white light mineral oil having a viscosity of about 50 to about 350 cSt and an average molecular weight of about 6800 g/mol, a nonionic surfactant, and polydimethylsiloxane. In some embodiments, the nonionic surfactant may comprise ethoxylated tridecyl alcohol.

In some embodiments, the compositions can include one or more carriers and/or diluents such as, for example, any solid or liquid carrier or diluent that is commonly used in pesticidal, agricultural, or horticultural compositions. Those skilled in the art will recognize that these components in a composition are typically referred to as "inert ingredients" and are regulated by the U.S. EPA. Suitably, any included additional carrier or diluent will not reduce the insecticidal efficacy of the composition, relative to the efficacy of the composition in the absence of the additional component.

Carriers and diluents can include, for example, solvents (e.g., water, alcohols, petroleum distillates, acids, and esters); vegetable oil (including but not limited to methylated vegetable oil); and/or plant-based oils as well as ester derivatives thereof (e.g., wintergreen oil, cedarwood oil, rosemary oil, peppermint oil, geraniol, rose oil, palmarosa oil, citronella oil, citrus oils (e.g., lemon, lime, and orange), dillweed oil, corn oil, sesame oil, soybean oil, palm oil, vegetable oil, olive oil, peanut oil, and canola oil). The composition can include varying amounts of other components such as, for example, fatty acids and fatty acid esters of plant oils (e.g., methyl palmitate/oleate/linoleate), and other auxiliary ingredients such as, for example, emulsifiers, dispersants, stabilizers, suspending agents, penetrants, coloring agents/dyes, UV-absorbing agents, and fragrances, as necessary or desired. The compositions may comprise carrier or diluent in an amount of at least about 1%, at least about 2%, or at least about 5% by weight of the composition. The compositions may comprise carrier or diluent in an amount of less than about 30%, less than about 25%, or less than about 20% by weight of the composition. The compositions may comprise carrier or diluent in an amount of about 1% to about 30%, about 2% to about 25%, or about 5% to about 20% by weight of the composition. Components other than mineral oil and coconut oil can be included in the compositions in any amount as long as the composition provides some amount of insecticidal efficacy.

Method of Making Compositions

The compositions can be generally prepared by any appropriate manufacturing processes and using any appropriate manufacturing equipment such as is known in the art. Suitably, the compositions can be prepared by combining the various components in an appropriate vessel (considering vessel size, amount of composition to be made and reactivity of components) with mixing (e.g., stirring) until a uniform or homogeneous composition is achieved. The various composition components can be added sequentially with stirring between each addition to ensure dissolution and/or dispersion of the previous component. This may be followed by addition of one or more additional components (e.g., solvents, diluents, and carriers) with stirring to provide a homogeneous composition.

Embodiments provide for the compositions manufactured as formulations that are useful for mosquito control. In some embodiments, the composition may be formulated for administration, application, or delivery to a surface of a body of water. Suitably, the composition can be formulated as a spray.

Methods

In other aspects, methods for mosquito control are provided. In some embodiments, methods may comprise contacting a mosquito with an effective amount of a composition comprising mineral oil, methylated coconut oil, at least one surfactant, and silicon, as described above.

Contacting may include contacting an insect directly or indirectly. For example, compositions described herein may be applied to a surface and an insect may subsequently or concurrently contact the surface and the composition. In some embodiments, compositions may be applied to a surface. In some embodiments, compositions may form a coating or film on a surface. In some embodiments, methods comprise forming a coating or film on a surface. The compositions can reduce the water's surface tension. The compositions may cause mosquito larvae to suffocate or drown. The compositions may prevent adult mosquitoes from laying eggs.

Surfaces may include, but are not limited to, surfaces of liquid such as bodies of water or other aquatic mosquito breeding sites. Examples of bodies of water and application sites include, without limitation, salt marshes, freshwater aquatic environments, storm water drainage areas, sewers and catch basins, woodland pools, snow pools, roadside ditches, retention ponds, freshwater dredge spoils, tire tracks, rock holes, pot holes, and similar areas subject to holding water; natural and manmade aquatic sites, fish ponds, ornamental ponds, fountains, and other artificial water-holding containers or tanks; flooded crypts, transformer vaults, abandoned swimming pools, construction, and other natural or manmade depressions; stream eddies, creek edges, detention ponds, freshwater swamps and marshes including mixed hardwood swamps, cattail marshes, common reed wetlands, water hyacinth ponds, and similar freshwater areas with emergent vegetation; brackish water swamps, marshes, and intertidal areas; sewage effluent, sewers, sewage lagoons, cesspools, oxidation ponds, septic ditches, and septic tanks; animal waste lagoons, settling ponds, livestock runoff lagoons, and wastewater impoundments associated with fruit and vegetable processing; and similar areas. Other examples include, without limitation, dormant rice fields (for application during the interval between harvest and preparation of the field for the next cropping cycle), standing water within pastures/hay fields, rangeland, orchards, and citrus groves where mosquito breeding occurs.

"Mosquito" is understood to refer to any specie of the ~3,500 species of the insect that is commonly associated with and given the common name "mosquito." Mosquitoes span 41 insect genera, including the non-limiting examples of *Aedes, Culex, Anopheles* (carrier of malaria), *Coquillettidia*, and *Ochlerotatus*. In embodiments described herein, a mosquito can refer to an adult mosquito or a larval mosquito, or both. Thus, some embodiments encompass methods or compositions wherein the insecticidal activity is as a mosquito "adulticide" or alternatively a mosquito "larvicide." Suitably, the compositions and methods described herein function as larvicides.

In some embodiments, the methods described herein can comprise any known route, apparatus, and/or mechanism for the delivery or application of the compositions and formulations. In some embodiments, the method comprises a sprayer. In some embodiments, compositions described herein may be applied at rates of about three gallons to about ten gallons per acre, depending on insect population densities. Traditional pesticide sprayers in the pest control markets are typically operated manually or electrically or are gas-controlled and use maximum pressures ranging from 15 to 500 psi generating flow rates from 1 gpm to 40 gpm.

For a composition to be registered and marketed as a "pesticide" within the United States for some uses (e.g. public health and pest control in residential structures), the U.S. EPA requires that a composition provide a minimum 95% insect mortality rate. In some embodiments, the composition is applied in an amount effective to kill at least about 95% of the contacted mosquito population. In some embodiments, the compositions provided herein have some degree of insecticidal activity, while not necessarily meeting the EPA requirements for an insecticide for certain uses. That is, certain compositions are still considered effective if less than about 95% of the contacted mosquito population is killed, as required by the EPA. In some embodiments, the composition is applied in an amount effective to kill at least about 90%, or less than about 95%, of the contacted mosquito population.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including but not limited to") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

EXAMPLES

Reference Example 1

Materials and Methods

Reagents.

Mineral oil was supplied by Brenntag Great Lakes, LLC (Wauwatosa, Wis.), Barton Solvents (Des Moines, Iowa), and Price Tech Group (Channahon, Ill.). Diluents were supplied by Stepan Company (Chicago, Ill.), Cognis Corporation (Ambler, Pa.), and Procter & Gamble Chemicals (Cincinnati, Ohio). Surface active agents were supplied by Akzo Nobel Surfactants (Chicago, Ill.), Stepan Company (Chicago, Ill.), Harcros Chemicals, Inc. (Joliet, Ill.), Huntsman Corporation (The Woodlands, Tex.), Croda Inc. (Edison, N.J.), and Dow Chemical (Midland, Mich.).

Laboratory Bioassay Method.

All larvae were reared on a diet of ground TETRAMIN® fish food (Tetra, Blacksburg, Va.) in an insectary maintained at 30° C. and 45% relative humidity (RH). Mainly third instars of *Aedes aegypti* were used for the laboratory container experiments. *Anopheles quadrimaculatus* and *Culex quinquefasciatus* were also tested where indicated.

Laboratory bioassays were conducted in 37.15" (I)×63.5" (w)×14.3" (d) plastic larval trays (laboratory containers). Each tray was filled with 27 liters of de-chlorinated water and received 50 healthy third instar larvae. The temperature of the water during most of the studies was 21° C. Additional testing was done at a water temperature of 15.6° C. and 28° C. Treatments were applied at a rate of 3 gal/acre or 663 µL/tray with an Eppendorf pipette. During the experimental period larvae were fed ground TETRAMIN® fish food (Tetra, Blacksburg, Va.) that was blended with water before introduction into the water of the larval tray to prevent flotation and thus interference with the surface film being tested.

Trays were scored for mortality at 1, 2, 4, 24, 48, and 72 hours following treatment introduction. At each time period the numbers of live and dead larvae were counted. Larvae were considered dead if they showed no movement including swimming/wriggling or filter feeding. Each treatment in the study was replicated three times using separate trays for each replication. A 95% mortality rate was considered acceptable for a commercial product.

The following calculations were made for testing a liquid larvicide in the laboratory at a field application rate of 3 gallons/acre:

$$3 \text{ gal/acre} \times 3.785 \text{ liters/gal} = 11.355 \text{ liters/acre}$$

$$11.355 \text{ liters/acre} \times 1000 \text{ mL/liter} = 11,355 \text{ mL/acre}$$

$$\frac{11,355 \text{ mL/acre}}{43,560 \text{ ft}^2/\text{acre}} = 0.26067 \text{ mL/ft}^2$$

$$\text{length} \times \text{width} = 25'' \times 14.64'' = 366.25 \text{ in}^2$$

-continued $$\frac{366.25 \text{ in}^2}{144 \text{ in}^2/\text{ft}^2} = 2.543 \text{ ft}^2$$

2.543 ft² × 0.26067 mL/ft² = 0.663 mL/tray = 663 μL/tray of liquid larvicide

Example 2

Compositions Containing Six Different Lots of Mineral Oil

A 50.00 g sample of liquid larvicide was prepared by adding 49.37 g (98.75% wt) white mineral oil, 0.48 g (0.95% wt) of a 4-mole ethoxylated nonylphenol (WITCONOL™ NP 40, Akzo Nobel Surfactants, Chicago, Ill.), and 0.15 g (0.30% wt) silicone oil to a 6 oz glass jar. The sample was mixed with an overhead stirrer at medium speed for 15 min. All samples were prepared with different lots of mineral oil and the same lot of the nonylphenol and silicone oil. Samples were tested using the Laboratory Bioassay Method (Reference Example 1).

TABLE 1

Comparative bioassay of six different lots of mineral oil on 3$^{rd}$ instar *Aedes aegypti* at 21° C.

| MINERAL OIL | % MORTALITY | | |
|---|---|---|---|
| | 24 HAT | 48 HAT | 72 HAT |
| Sample 1 | 100 | 100 | 100 |
| Sample 2 | 10 | 33 | 47 |
| Sample 3 | 31 | 82 | 84 |
| Sample 4 | 6 | 35 | 50 |
| Sample 5 | 59 | 93 | 96 |
| Sample 6 | 37 | 81 | 87 |

* HAT = Hours After Treatment (hours after liquid larvicide (treatment) is applied to the surface of the water).

According to the results shown in Table 1, the compositions were effective in controlling *Aedes aegypti* mosquitoes at 21° C., but with variable efficacy.

Example 3

Compositions Having Varying HLB Numbers

Surfactants with different HLB numbers were tested in an effort to reduce the variable efficacy of the compositions demonstrated in Example 2.

Consistent with the compositions tested in Example 2, a 50.00 g sample of liquid larvicide was prepared by adding 49.37 g (98.75%) of white mineral oil, 0.48 g (0.95%) of an ethoxylated nonylphenol (WITCONOL™ NP Series, Akzo Nobel Surfactants, Chicago, Ill.), and 0.15 g (0.30%) silicone oil to a 6 oz glass jar. The sample was mixed with an overhead stirrer at medium speed for 15 min. All samples were prepared with one lot of mineral oil, one lot of silicone oil, and an ethoxylated nonylphenol from the WITCONOL™ Series of surfactants with an increasing HLB number. In addition to the screening of each WITCONOL™ surfactant as illustrated in Table 2, a second series of blends of WITCONOL™ surfactants was also tested for biological activity, as shown in Table 3. Samples were tested using the Laboratory Bioassay Method (Reference Example 1).

TABLE 2

Comparative Bioassay of Six WITCONOL ™ NP Series Surfactants on 3$^{rd}$ instar *Aedes aegypti* at 21° C.

| Composition | Witconol No. | HLB | % Mortality | | |
|---|---|---|---|---|---|
| | | | 24 HAT | 48 HAT | 72 HAT |
| Sample 7 | NP 15 | 4.6 | 3 | 18 | 47 |
| Sample 8 | NP 20 | 6.9 | 0 | 5 | 21 |
| Sample 9 | NP 40 | 8.9 | 1 | 31 | 53 |
| Sample 10 | NP 60 | 10.9 | 1 | 11 | 27 |
| Sample 11 | NP 90 | 13.0 | 1 | 8 | 16 |
| Sample 12 | NP 100 | 13.1 | 3 | 13 | 31 |

TABLE 3

Comparative Bioassay of Six WITCONOL ™ NP Series Blends of Surfactants on 3$^{rd}$ instar *Aedes aegypti* at 21° C.

| Composition | WITCONOL ™ No. Blend (50/50) | HLB (calculated) | % Mortality | | |
|---|---|---|---|---|---|
| | | | 24 HAT | 48 HAT | 72 HAT |
| Sample 13 | NP 15/20 | 5.7 | 0 | 12 | 29 |
| Sample 14 | NP 20/40 | 7.9 | 2 | 7 | 27 |
| Sample 15 | NP 15/90 | 8.8 | 5 | 27 | 42 |
| Sample 16 | NP 40/60 | 9.9 | 1 | 9 | 17 |
| Sample 17 | NP 40/90 | 10.9 | 0 | 15 | 42 |
| Sample 18 | NP 40/100 | 11.0 | 0 | 24 | 44 |
| Sample 19 | NP 60/90 | 11.9 | 3 | 11 | 21 |
| Sample 20 | NP 60/100 | 12.0 | 0 | 7 | 44 |
| Sample 21 | NP 90/100 | 13.1 | 0 | 7 | 20 |

As shown in Tables 2 and 3, changing the surfactant (increasing the HLB number) to make the blend less lipophilic did not produce an efficacious composition. It was determined that this class of surfactants (alkyl nonylphenols) would not provide the 95% mortality as required by the EPA. After screening a number of different nonionic surfactant chemistries, it was further determined that a change in surfactant would not alter the composition enough to overcome the variation in efficacy.

Example 4

Compositions Containing Methylated Coconut Oil (MCO)

Methylated coconut oil (MCO) was tested as a diluent/cosolvent for mineral oil in the compositions in the examples above. As an alternative to conventional chemistries, essential oils such as MCO are "natural" or derived from plants, and they can advantageously provide a level of safety both to humans and to the environment. It was determined that MCO was soluble in all components of the initial composition and could provide added benefits (both safety and efficacy) when mixed with mineral oil, a surfactant, and silicone oil.

A series of samples was prepared as set forth in Example 2 with 0.95% WITCONOL™ NP-40 (Akzo Nobel Surfactants, Chicago, Ill.) and 0.30% silicone oil, with varying amounts of mineral oil and MCO (STEPAN® C-42, Stepan Company, Chicago, Ill.) as indicated in Table 4. In all samples, the amount of WITCONOL™ surfactant and silicone oil was held constant. Samples were tested using the Laboratory Bioassay Method (Reference Example 1).

TABLE 4

Comparative Bioassay of Mineral Oil/MCO/silicone oil on 3$^{rd}$ instar *Aedes aegypti* at 21° C.

| Composition | Wt % Mineral oil | Wt % MCO | % Mortality | | |
|---|---|---|---|---|---|
| | | | 24 HAT | 48 HAT | 72 HAT |
| Sample 22 | 50.00 | 48.75 | 9 | 25 | 63 |
| Sample 23 | 25.00 | 73.75 | 19 | 73 | 93 |
| Sample 24 | 12.50 | 86.25 | 63 | 90 | 97 |
| Sample 25 | 10.00 | 88.75 | 83 | 97 | 100 |
| Sample 26 | 5.00 | 93.75 | 91 | 98 | 100 |
| Sample 27 | 2.50 | 96.25 | 84 | 95 | 97 |
| Sample 28 | 1.00 | 97.75 | 88 | 99 | 99 |

It was surprisingly found that the addition of a methylated coconut oil to the composition provided a consistent level of insect control when applied to the surface of a body of water. Additionally, the amount of mineral oil could be reduced to a range of from about 5% to 10% and still maintain an efficacious treatment.

Example 5

Compositions Evaluating the Effects of Various Surfactant Types

A series of screening bioassays was initiated to find the optimum surfactant for the mineral oil/MCO/silicone oil blend in Example 4 and to also replace the nonylphenol surfactant. The replacement of the nonylphenol surfactant would have human health and environmental benefits. Replacing the nonylphenol surfactant would be additionally advantageous because it has been banned in the European Union since May 2005 and is under review by the U.S. EPA.

Consistent with Example 2, a series of 50.00 g samples was prepared to evaluate the effectiveness of a group of surfactants to replace the nonylphenol surfactant (WITCONOL™ NP Series, Akzo Nobel Surfactants, Chicago, Ill.). Each sample contained 10.00% mineral oil, 88.75% MCO, 0.30% silicone oil, and 0.95% of the selected surfactant, as shown in Table 5. Samples were tested using the Laboratory Bioassay Method (Reference Example 1).

TABLE 5

Comparative bioassay of surfactant types in a composition on 3$^{rd}$ instar *Aedes aegypti* at 21° C.

| Composition | Surfactant Types | HLB | % Mortality | | |
|---|---|---|---|---|---|
| | | | 24 HAT | 48 HAT | 72 HAT |
| Sample 29 | sorbitan trioleate | 1.8 | 49 | 86 | 91 |
| Sample 30 | sorbitan monooleate | 4.3 | 81 | 100 | 100 |
| Sample 31 | sorbitan monolaurate | 8.6 | 83 | 99 | 99 |
| Sample 32 | sorbitan trioleate | 11.0 | 21 | 71 | 83 |
| Sample 33 | ethoxylated vegetable oil | 12.0 | 6 | 36 | 59 |
| Sample 34 | ethoxylated tridecyl alcohol | 12.8 | 75 | 97 | 98 |
| Sample 35 | sorbitan monostearate | 14.9 | 66 | 93 | 99 |
| Sample 36 | sorbitan monooleate | 15.0 | 75 | 95 | 99 |
| Sample 37 | sorbitan monolaurate | 16.7 | 40 | 91 | 100 |

The ethoxylated tridecyl alcohol (SURFONIC® TDA-8, Huntsman Corporation, The Woodlands, Tex.) proved to be the most versatile surfactant in this series due to its ability to work over a wide range of temperature, pH, and water hardness (data not shown) and therefore was chosen as the preferred surfactant.

Example 6

Comparative Bioassay of Varying Levels of Ethoxylated Tridecyl Alcohol

A series of 50.00 g samples was prepared according to Example 2, with varying amounts of ethoxylated tridecyl alcohol surfactant. The amount of mineral oil was maintained at 10.00%, and the amount of silicone oil was maintained at 0.30% in each of the sample preparations. The weight % of the MCO was adjusted accordingly to the weight % of ethoxylated tridecyl alcohol (SURFONIC® TDA-8, Huntsman Corporation, The Woodlands, Tex.) to give a 100% composition, as shown in Table 6. Samples were tested using the Laboratory Bioassay Method (Reference Example 1).

TABLE 6

Comparative bioassay of level of ethoxylated tridecyl alcohol in a composition on 3$^{rd}$ instar *Aedes aegypti* at 21° C.

| Composition | Wt % MCO | Wt % SURFONIC® TDA-8 | % Mortality | | |
|---|---|---|---|---|---|
| | | | 24 HAT | 48 HAT | 72 HAT |
| Sample 38 | 88.20 | 1.50 | 83 | 97 | 100 |
| Sample 39 | 87.70 | 2.00 | 81 | 96 | 100 |
| Sample 40 | 85.70 | 4.00 | 89 | 97 | 100 |
| Sample 41 | 84.70 | 5.00 | 83 | 98 | 100 |

A 4% level of ethoxylated tridecyl alcohol was determined to be the most efficacious and economical treatment in this study, as exemplified by Sample 40 at 10.00% mineral oil, 85.70% MCO, 4.00% SURFONIC® TDA-8, and 0.30% silicone oil.

Example 7

Evaluation of Sample 40 at Varying Temperatures

When applying a liquid larvicide to shallow aquatic breeding sites, typical water temperatures may range from 60° F. to 80° F. Therefore, Sample 40 (Example 6) was tested at three water temperatures at a field rate of 3 gallons per acre as described in the Laboratory Bioassay Method (Reference Example 1).

Using a chilled water bath, Sample 40 was tested at a water temperature of 15.6° C. (60° F.). Only one replication (50 larvae) was tested, and the mortality was 86% at 24 hours, 96% at 48 hours, and 98% at 72 hours. Sample 40 was tested in three replicates of 50 larvae each (total 150) at 21° C. (70° F.), and the mean mortality was 74% at 24 hours, 96% at 48 hours, and 99.33% at 72 hours. Using an elevated temperature water bath, Sample 40 was tested in one replicate (50 larvae) at a water temperature of 27° C. (80° F.), and the mortality was 72% at 24 hours, 98% at 48 hours, and 98% at 72 hours. The % mortality of the composition was acceptable throughout a range of water temperatures that may be encountered when applying the liquid larvicide at a commercial application rate of 3 gallons/acre.

Example 8

Evaluation of Sample 42 on *Aedes aegypti*, *Anopheles quadrimaculatus*, and *Culex quinquefasciatus*

In addition to being able to provide an efficacious treatment over a range of water temperatures, a composition was tested for efficacy in controlling other genera of mosquito larvae. There are 41 genera of mosquitoes containing approximately 3500 species, with some of the most common being *Aedes, Culex*, and *Anopheles*. These larvae were tested in the laboratory using a composition similar to Sample 40, but with the substitution of a higher molecular weight silicone oil (>6800 g/mole). While the viscosity of the silicone oil increased from 50 cSt to 350 cSt, this did not affect the physical or biological performance of the composition. The higher molecular weight silicone oil had the added advantage of being U.S. EPA compliant under 40 CFR 180.960 (polymer exempt from the requirement of a tolerance on growing crops pre and post harvest). This is a significant advantage for the applicator of a surface oil for the control of mosquito larvae, particularly when spraying in close proximity to growing crops.

The weight % of each component remained the same. A 50.00 g sample was prepared as in Example 2 using 10.0% mineral oil, 85.7% methylated coconut oil (STEPAN® C-42, Stepan Company, Chicago, Ill.), 4.0% ethoxylated tridecyl alcohol (SURFONIC® TDA-8, Huntsman Corporation, The Woodlands, Tex.), and 0.3% polydimethylsiloxane polymer (XIAMETER® PMX-200 Fluid, either 350 cSt or 50 cSt from Dow Chemical, Midland, Mich.). The sample was referred to as Sample 42 and was tested using the Laboratory Bioassay Method (Reference Example 1).

TABLE 7

Comparative bioassay of Sample 42 at 21° C.

| | | % MORTALITY | | |
|---|---|---|---|---|
| Composition | Larvae | 24 HAT | 48 HAT | 72 HAT |
| Sample 42 | *Aedes aegypti* | 76 | 84 | 90 |
| Sample 42 | *Anopheles quadrimaculatus* | 90 | 98 | 100 |
| Sample 42 | *Culex quinquefasciatus* | 100 | 100 | 100 |

Sample 42 was determined to be excellent in controlling *Culex quinquefasciatus* as well as providing an efficacious treatment for *Aedes aegypti* and *Anopheles quadrimaculatus*. No differences in efficacy were observed as a result of the substitution of the low molecular weight silicone oil.

Example 9

Evaluation of Various Suppliers and Fractions of MCO

A 50.00 g sample of each of the candidate methyl esters of coconut oil (85.7%) was prepared with 10.00% mineral oil, 4.0% ethoxylated tridecyl alcohol (SURFONIC® TDA-8, Huntsman Corporation, The Woodlands, Tex.), and silicone oil at 0.3% (polydimethylsiloxane polymer, XIAMETER® PMX-200 Fluid, from Dow Chemical, Midland, Mich.). Samples were tested using the Laboratory Bioassay Method (Reference Example 1).

TABLE 8

Comparative efficacy of compositions containing methyl esters of coconut oil provided by various suppliers at 21° C.

| | | | % Mortality | | |
|---|---|---|---|---|---|
| Composition | MCO | Type * | 24 HAT | 48 HAT | 72 HAT |
| Sample 43 | P&G CE-810 | C8-C10 | 10 | 39 | 63 |
| Sample 44 | P&G CE-1095 | C8-C10 | 39 | 70 | 77 |
| Sample 45 | STEPAN ® C-42 | C12-C14 | 87 | 100 | 100 |
| Sample 46 | P&G CE-1270 | C12-C14 | 81 | 97 | 100 |
| Sample 47 | P&G CE-1295 | C12-C14 | 93 | 99 | 100 |
| Sample 48 | Aqnique ME 1270-U | C12-C14 | 89 | 98 | 100 |
| Sample 49 | STEPAN ® C-65 | C16-C18 | 41 | 85 | 97 |
| Sample 50 | P&G CE-1618 | C16-C18 | 96 | 100 | 100 |

* The methyl esters are fractionated for different end use applications: $C_8$-$C_{10}$ would be considered a light cut; $C_{12}$-$C_{14}$ would be considered a mid cut; and $C_{16}$-$C_{18}$ would be considered a heavy cut.

Example 10

Freeze-Thaw Cycle Test

A 10.0 g sample of Sample 42 (Example 8) was weighed into a 25 mL glass vial and placed in a freezer for 16 hours at 0° C. The sample was removed from the freezer and allowed to sit at room temperature for 8 hours. Observations were reported, the sample was placed back in the freezer, and this cycle of freezing and thawing was repeated for a total of 3 cycles. The composition showed no signs of crystallization after 3 freeze thaw cycles.

Example 11

Evaluation of Each Component in Sample 42

The individual components of Sample 42 (Example 8) were tested for activity against mosquitoes. No sample preparation was required because each component was tested neat ("as is"). Testing was done using the Laboratory Bioassay Method (Reference Example 1).

TABLE 9

Comparative bioassay of the components in Sample 42 on $3^{rd}$ instar *Aedes aegypti* at 21° C.

| | | % MORTALITY | | |
|---|---|---|---|---|
| Component | Rate | 24 HAT | 48 HAT | 72 HAT |
| Mineral oil | 663 µL | 0 | 0 | 1 |
| MCO (STEPAN ® C-42) | 663 µL | 7 | 7 | 9 |
| ethoxylated tridecyl alcohol (SURFONIC ® TDA-8) | 663 µL | 17 | 20 | 25 |
| polydimethylsiloxane polymer (XIAMETER ® PMX-200 Fluid, 350 cSt) | 663 µL | 2 | 3 | 24 |

Separately, each component in Sample 42 when tested at a field application rate of 3 gallons/acre (663 µL per tray) exhibited very low biological activity. When combined in an optimum ratio as defined in Sample 42 (Example 8), however, the components provided an efficacious treatment across a range of water temperatures and common mosquito larvae.

Example 12

Evaluation of Methylated Coconut Oil with Four Different Lots of Mineral Oil

Four samples (50.00 g each) of Sample 42 (Example 8) was prepared containing (85.7%) methylated coconut oil (STEPAN® C-42, Stepan Company, Chicago, Ill.) with 10.0% mineral oil (various suppliers), 4.0% ethoxylated tridecyl alcohol (SURFONIC® TDA-8, Huntsman Corporation, The Woodlands, Tex.), and silicone oil at 0.3% (polydimethylsiloxane polymer, XIAMETER® PMX-200 Fluid, 350 cSt, from Dow Chemical, Midland, Mich.). Each sample contained a different lot of mineral oil. Samples were tested using the Laboratory Bioassay Method (Reference Example 1).

TABLE 10

Comparative bioassay of 4 different lots of mineral oil on 3$^{rd}$ instar *Aedes aegypti* at 21° C.

| | % MORTALITY | | |
|---|---|---|---|
| Variable | 24 HAT | 48 HAT | 72 HAT |
| Mineral oil A | 89 | 97 | 100 |
| Mineral oil B | 87 | 100 | 100 |
| Mineral oil C | 96 | 96 | 100 |
| Mineral oil D | 93 | 100 | 100 |

When compared to the results in Table 1, the percent mortality is consistent across four different lots of mineral oil. The compositions provide >95% mortality within 48 hours after treatment (HAT), independent of the lot of mineral oil used.

Example 13

Field Study

The efficacy of Sample 42 (Example 8) was examined with a larval bioassay. *Aedes aegypti* and *Culex quinquefasciatus* 3$^{rd}$ instar were exposed to Sample 42 at a rate of 2.39 mL/pool (equivalent to 3 gal/acre). Experiments were conducted in PVC pools (41 inch diameter, 5 inches deep) filled with approximately three inches of well water. Treatments included Sample 42 and an untreated control with four replicates.

Materials and Methods.

Experiments were conducted under field conditions with water temperatures of 69-73.9° F. and ambient air temperatures ranging from 57.3° F. at night to 82.3° F. during the day at the Clarke Technical field research site in Bronson, Fla. Only a trace of rain was recorded during the trial. The mosquito species and life stage studied was *Aedes aegypti* and *Culex quinquefasciatus* 3$^{rd}$ instars obtained from the Clarke insectary. All larvae were visually inspected to document instar and species.

Experiments were conducted in PVC pools (41 inches in diameter and 5 inches deep) filled with three inches of well water. All pools were allowed to acclimate for 24 hours before testing. Sample 42 was applied at a rate of 2.39 mL to each treatment pool following the introduction of the larvae.

The larval challenge set consisted of 20 *Aedes aegypti* and 20 *Culex quinquefasciatus* healthy 3$^{rd}$ instar larvae and were allowed to free range throughout the pool. Pools were scored for mortality at 24 hours and 48 hours post larval introduction. Dead larvae were removed from each pool at each scoring period. Larvae were considered dead if they exhibited no movement including swimming, wriggling or filter feeding.

Larvae used for this study were reared on a diet of ground TETRAMIN® fish food (Tetra, Blacksburg, Va.). All larvae were reared at 28-30° C., 44-48% RH, and 12/12 light/dark photoperiod in the Clarke insectary. All larvae were visually inspected for accuracy of age and species identification.

RESULTS AND CONCLUSIONS

The summary data for the comparison is reported in Tables 11 and 12. This field study demonstrated that Sample 42 resulted in 90% insect mortality at 24 hours after treatment and 100% mortality after 48 hours after treatment at a commercial application rate of 3 gal/acre. A second comparison was not required because the first comparison demonstrated 100% mortality after 48 hours.

TABLE 11

*Aedes aegypti* and *Culex quinquefasciatus* 24 hour summary data for Sample 42 pool efficacy trial.

| Challenge Set | Treatment | Mean Mortality (SE)1 | % Mortality |
|---|---|---|---|
| 1 | Sample 42 | 36.0 (0.913)a | 90.00 |
| 1 | Untreated Control | 0.5 (0.5)b | 1.25 |

1Means followed by the same letter are not significantly different P < 0.005); mean separation by LSD ($\alpha$ = 0.05), within each challenge set.

TABLE 12

*Aedes aegypti* and *Culex quinquefasciatus* 48 hour summary data for Sample 42 pool efficacy trial.

| Challenge Set | Treatment | Mean Mortality (SE)1 | % Mortality |
|---|---|---|---|
| 1 | Sample 42 | 40.0 (0.00)c | 100.00 |
| 1 | Untreated Control | 1.75 (0.75)d | 4.38 |

1Means followed by the same letter are not significantly different P < 0.005); mean separation by LSD ($\alpha$ = 0.05), within each challenge set.

The invention claimed is:

1. A composition effective for mosquito control, said composition comprising:
   i) about 5% to about 15% mineral oil;
   ii) about 70% to about 90% methylated coconut oil;
   iii) about 1% to about 10% surfactant; and
   iv) about 0.2% to about 4% silicone;
wherein said composition reduces a mosquito population treated therewith by at least about 95%.

2. The composition of claim 1, wherein the silicone comprises polydimethylsiloxane.

3. The composition of claim 1, wherein the surfactant comprises a nonionic surfactant.

4. The composition of claim 3, wherein the nonionic surfactant comprises ethoxylated tridecyl alcohol.

5. The composition of claim 1, wherein the mineral oil is present in an amount of about 8% to about 12% by weight.

6. The composition of claim 1, wherein the methylated coconut oil is present in an amount of about 80% to about 90% by weight.

7. The composition of claim 1, wherein the at least one surfactant is present in an amount of about 3% to about 6% by weight.

8. The composition of claim 1, wherein the silicone is present in an amount of about 0.2% to about 0.4% by weight.

9. The composition of claim 1, wherein the composition excludes nonylphenol surfactants.

10. A composition effective for mosquito control, said composition comprising about 8% to about 12% mineral oil, about 80% to about 90% methylated coconut oil, about 3% to about 6% nonionic surfactant, and about 0.2% to about 0.4% polydimethylsiloxane; wherein said composition reduces a mosquito population treated therewith by at least about 95%.

11. A formulation comprising the composition of claim 1, wherein the formulation is in the form of a spray.

12. A method for mosquito control comprising applying a composition to a surface of a body of water; wherein said composition comprises:
   i) about 5% to about 15% mineral oil;
   ii) about 70% to about 90% methylated coconut oil;
   iii) about 1% to about 10% surfactant; and
   iv) about 0.2% to about 4% silicone.

13. The method of claim 12, wherein the composition forms a coating on the surface of the water.

14. The method of claim 12, wherein the composition is applied in an amount effective to kill at least about 95% of the mosquito population.

15. The method of claim 12, wherein the mosquito control comprises killing mosquito larvae in or on the body of water.

16. The method of claim 12, wherein the mosquito control comprises inhibiting adult mosquitoes from laying eggs in or on the body of water.

17. The method of claim 12, wherein the mosquito is any mosquito of the genus *Aedes, Culex*, or *Anopheles*.

\* \* \* \* \*